(12) United States Patent
Kopreski

(10) Patent No.: US 7,785,842 B2
(45) Date of Patent: *Aug. 31, 2010

(54) COMPARATIVE ANALYSIS OF EXTRACELLULAR RNA SPECIES

(75) Inventor: Michael S. Kopreski, Long Valley, NJ (US)

(73) Assignee: OncoMEDx, Inc., Long Valley, NJ (US)

( * ) Notice: Subject to any disclaimer, the term of this patent is extended or adjusted under 35 U.S.C. 154(b) by 441 days.

This patent is subject to a terminal disclaimer.

(21) Appl. No.: 11/346,590

(22) Filed: Feb. 2, 2006

(65) Prior Publication Data

US 2006/0228729 A1    Oct. 12, 2006

Related U.S. Application Data

(63) Continuation-in-part of application No. 10/658,873, filed on Sep. 5, 2003, which is a continuation-in-part of application No. 10/013,868, filed on Oct. 30, 2001, now Pat. No. 6,939,671, which is a continuation of application No. 09/155,152, filed as application No. PCT/US97/03479 on Mar. 14, 1997, now Pat. No. 6,329,179.

(60) Provisional application No. 60/014,730, filed on Mar. 26, 1996.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .................. 435/91.2; 435/6; 435/91.1; 536/23.1; 536/24.3; 536/24.33; 536/25.3

(58) Field of Classification Search .............. 435/6, 435/91.1, 91.2, 183; 436/94, 501; 536/23.1, 536/24.3, 24.33, 25.3, 25.32
See application file for complete search history.

(56) References Cited

U.S. PATENT DOCUMENTS

| | | | |
|---|---|---|---|
| 4,350,156 A | 9/1982 | Malchesky | |
| 4,631,130 A | 12/1986 | Watanabe | |
| 4,683,195 A | 7/1987 | Mullis et al. | |
| 4,699,877 A | 10/1987 | Cline et al. | |
| 4,738,927 A * | 4/1988 | Taniguchi et al. | 435/243 |
| 4,874,853 A | 10/1989 | Rossi | |
| 4,874,858 A | 10/1989 | Magistro | |
| 4,999,290 A | 3/1991 | Lee | |
| 5,019,243 A | 5/1991 | McEwen et al. | |
| 5,087,617 A | 2/1992 | Smith | |
| 5,098,890 A | 3/1992 | Gerwitz et al. | |
| 5,124,246 A | 6/1992 | Urdea et al. | |
| 5,155,018 A | 10/1992 | Gillespie et al. | |
| 5,217,889 A | 6/1993 | Roninson et al. | |
| 5,274,087 A | 12/1993 | Barnett et al. | |
| 5,300,635 A | 4/1994 | Macfarlane | |
| 5,409,818 A | 4/1995 | Davey et al. | |
| 5,429,923 A | 7/1995 | Seidman | |
| 5,436,318 A | 7/1995 | Reyes et al. | |
| 5,470,724 A | 11/1995 | Ahern | |
| 5,506,106 A | 4/1996 | Croce | |
| 5,532,220 A | 7/1996 | Lee | |
| 5,576,178 A | 11/1996 | Emanuel | |
| 6,001,987 A | 12/1999 | Perron | |
| 6,051,374 A | 4/2000 | Simons | |
| 6,057,105 A | 5/2000 | Hoon | |
| 6,329,179 B1 | 12/2001 | Kopreski | |
| 6,344,317 B2 | 2/2002 | Urnovitz | |
| 6,607,898 B1 * | 8/2003 | Kopreski et al. | 435/91.2 |
| 6,656,704 B1 | 12/2003 | Komeluk et al. | |
| 6,759,217 B2 * | 7/2004 | Kopreski | 435/91.2 |
| 6,794,135 B1 * | 9/2004 | Kopreski et al. | 435/6 |
| 6,916,634 B2 * | 7/2005 | Kopreski | 435/91.2 |
| 6,939,671 B2 * | 9/2005 | Kopreski | 435/6 |
| 2004/0014079 A1 | 1/2004 | Kopreski et al. | |
| 2004/0058331 A1 | 3/2004 | Akagi | |
| 2006/0286578 A1 | 12/2006 | Kopreski et al. | |
| 2008/0096217 A1 | 4/2008 | Kopreski | |
| 2008/0207723 A1 | 8/2008 | Kopreski | |

FOREIGN PATENT DOCUMENTS

| | | |
|---|---|---|
| DE | 3717212 A1 | 8/1988 |
| DE | 3717212 | 9/2003 |
| WO | 9009456 A1 | 8/1990 |

(Continued)

OTHER PUBLICATIONS

Schrader et al., The differentiation status of primary gonadal germ cell tumors correlates inversely with telomerase activity and the expression level of the gene encoding the catalytic subunit of telomerase. BMC Cancer, 2, 32, 2002.*

(Continued)

*Primary Examiner*—Frank W Lu
(74) *Attorney, Agent, or Firm*—McDonnell Boehnen Hulbert & Berghoff LLP

(57) ABSTRACT

The invention provides methods, reagents and kits for enabling comparative analysis of extracellular RNA species in bodily fluids including plasma and serum to detect, infer, or monitor cancer and other neoplasia.

13 Claims, No Drawings

FOREIGN PATENT DOCUMENTS

| WO | WO 90/09456 A1 | 8/1990 |
|---|---|---|
| WO | 97/35589 A | 10/1997 |
| WO | 98/14617 A | 10/1997 |
| WO | 98/14617 A1 | 4/1998 |
| WO | 99/67397 | 12/1999 |

OTHER PUBLICATIONS

Rohde et al., Expression of the Human Telomerase Reverse Transcriptase Is Not Related to Telomerase Activity in Normal and Malignant Renal Tissue. Clinical Cancer Research, 6, 4803-4809, 2000.*

Guin et al., Electrophoretic Characterization of Plasma RNA. Biochemical Medicine, 13, 224-230, 1975.*

Abravaya et al., "Detection of point mutations with a modified ligase chain reaction (GAP-LCR)," *Nucleic Acids Research* 23:675-682 (1995).

Alkema et al., "Characterization and Chromosamal Localization of the Human Prata-Oncogene BMI-1," *Human Mol Genet* 2:1597-1603 (1993).

Aoki et al., "Liposome-mediated in viva gene transfer on antisense K-ras construct inhibits pancreatic tumor dissemination in the murine peritoneal cavity," *Cancer Research* 55:3810-3816 (1995).

Barz et al., "Characterization of Cellular and Extracellular Plasma Membrane Vesicles from a Non-metastasing Lymphoma (Eb) and Its Metastasing Variant (Esb)," *Biochin Biophys Acta* 814:77-84 (1985).

Bauer et al., "Identification of H-2Kb Binding and Immunogenic Peptides from Human Papillama Virus Tumour Antigens E6 and E7," *Scand J Immunol* 42:317-323 (1995).

Blackburn et al., "Electrochemiluminescence detection for development of immunoassays and DNA probe assays for clinical diagnostics," *Olin Chem* 37/9:1534-1539 (1991).

Bobo et al., "Diagnosis of chlamydia trachomatis cervical infection by detection of amplified DNA with an enzyme immunoassay," *J din Micra* 28:1968-1973 (1990).

Bocchia et al., "Specific Binding of Leukemia Oncogene Fusion Peptides to HLA Class I Molecules," *Blood* 85:2680-2684 (1995).

Boom et al., "Rapid and Simple Method for Purification of Nucleic Acids," *J Clin Micro* 28:495-503 (1990).

Boom et al., "Rapid Purification of Hepatitis B Virus DNA from Seruc," *J Clin Micro* 29:180-181 (1991).

Brossart et al., "Detection of residual tumor cells in patients with malignant melanoma responding to immunotherapy," *J Immunotherapy* 15:38-41 (1994.

Buchman et al., "Selective RNA amplification: A novel method using d UMP-containing primers and uracil DNA glycosylase," *PCR Methods Applic* 3:28-31 (1993).

Carr et al., "Circulating Membrane Vesicles in Leukemic Blood," *Cancer Research* 45:5944-5951 (1985).

Cheung et al., "Rapid and Sensitive Method for Detection of Hepatitis C Virus RNA by Using Silica Particles," *J Clin Micro* 32:2593-2597 (1994).

Chirgwin et al., "Isolation of biologically active ribonucleic acid from sources enriched in ribonuclease," *Biochemistry* 18:5294-5299 (1979).

Chomczynski and Mackey, "Modification of the TRI reagent (TM) procedure for isolation of RNA from polysaccaride- and proteaglycan-rich sources," *BioTechniques* 19:942-945 (1995).

Chomczynski and Mackey, "Substitution of chloroform by bromochloropropane in the single-step method of RNA isolation," *Analytical Biochemistry* 225:163-164 (1995).

Chomczynski et al., "Single-step method of RNA isolation by acid guanidinium thiocyanate-phenol-chloroform extraction," *Analytical Biochemistry* 162:156-159 (1987).

Chomczynski, "A reagent for the single-step simultaneous isolation of RNA, DNA and proteins from cell and tissue samples," *Biotech* 15:532-537 (1993).

Chu et al., "Thymidylate synthase binds to c-myc RNA in human colon cancer cells and in vitro," *Mol Cell Biol* 15:179-185 (1995).

Cohen, "Biochemical Therapy: Antisense Compounds," *In: Biologic Teraphy of Cancer*(DeVita, Hellman, Rosenberg, eds) J.B. Lippincott, Ca., Philadelphia (1991) pp. 763-775.

Colomer et al., "erB-2 antisense oligonucleotides inhibit the proliferation of breast carcinoma cells with erb-2 oncogene amplification," *Br J Cancer* 70:819-825 (1994).

Coutlee et al., "Immunodetection of DNA with biotinylated RNA probes: A study of reactivity of a monoclonal antibody to DNA-RNA hybrids," *Analytical Biochemistry* 181:96-105 (1989).

Datta et al., "Sensitive Detection of Occult Breast Cancer by the Reverse-transcriptase Polymerase Chain Reaction," *Journal of Clinical Oncology* 12:475-482 (1994).

Davidova and Shapot, "Liporibonucleoprotein Complex as an Integral Part of Animal Cell Plasma Membranes," *FEBS Lett* 6:349-351 (1970).

DiCesare et al., "A high-sensitivity electrochemiluminescense-based detection system for automated PCR product quantitation," *BioTechniques* 15:152-157 (1993).

Doi et al., "Detection of beta-human chorionic ganadotropin mRNA as a marker for cutaneoud malignant melanoma," *Int J Cancer* 65:454-45- (1996).

Dosaka et al., "A complex pattern of translational initiation and phosphorylation in L-Myc Proteins," *Oncogene* 6:371-378 (1991).

Edmands et al., "Rapid RT-PCR Amplification from Limited Cell Numbers," *PCR Methods Applic* 3:317-319 (1994).

Feng et al., "The RNA component of human telomerase," *Science* 269:1236-1241 (1995).

Fournie et al., "Recovery of nanogram quantities of DNA from plasma and quantitative measurement using labeling by nick translation," *Analytical Biochemistry* 158:250-256 (1986).

Gerhard et al., "Specific detection of carcinoembryonic antigen-expressing tumor cells in bone marrow aspirates by polymerase chain reaction," *J Clin Oncol* 12:725-729 (1994).

Ghossein et al., "Detection of Circulating Tumor Cells in Patients with Localized and Metastatic Prostatic Carcinoma: Clinical Implications," *Journal of Clinical Oncology* 13:1195-1200 (1995).

Higashiyama et al., "Reduced Motility Related Protein-1 (MRP-1/CD9) Gene Expression as a Factor of Poor Prognosis in Non-small Cell Lung Cancer," *Cancer Research* 55:6040-6044 (1995).

Hoon et al., "Detection of occult melanoma cells in blood with a multiple-marker polymerase chain reaction assay," *J Clin Oncol* 13:2109-2116 (1995).

Hoover et al., "Immunatherapy by Active Specific Immunization: Clinical Applications," *In: Biologic-Therapy of Cancer* (DeVita, Hellman, Rosenberg, eds) J.B. Lippincott, Co., Philadelphia (1991) pp. 670-682.

Imai et al., "Detection of HIV-1 RNA in Heparinized Plasma of HIV-1 Seropositive Individuals," *J Virol Methods* 36:181-184 (1992).

Jrdea et al., "Direct and quantitative detection of HIV-I RNA in human plasma with a branched DNA signal amplification assay," *AIDS* 7(suppl 2):S11-514 (1993).

Juckett and Rosenberg, "Actions of Cis-diamminedichloroplatinum on Cell Surface Nucleic Acids in Cancer Cells as Determined by Cell Electrophoresis Techniques," *Cancer Research* 42:3565-3573 (1982).

Kahn et al., "Rapid and sensitive nonradioactive detection of mutant K-ras genes via enriched PCR amplification," *Oncogene* 6:1079-1083 (1991).

Kamm and Smith, "Nucleic acid concentrations in normal human plasma," *Clinical Chemistry* 18:519-522 (1972).

Karet et al., "Quantification of mRNA in human tissue using fluorescent nested reverse-transcriptase polymerase chain reaction," *Analytical Biochemistry* 220:384-390 (1994).

Katz et al., "Enhanced Reverse Transcriptase-Polymerase Chain Reaction for Prostate Specific Antigen as a Indicator of True Pathologic Stage in Patients with Prostate Cancer," *Cancer* 75:1642-1648 (1995).

Kievits et al., "NASBA(TM) isothermal enzymatic in vitro nucleic acid amplification optimized for the diagnosis of HIV-1 infection," *J Virological Methods* 35:273-286 (1991).

Kim et al., "Specific association of human telomerase activity with immortal cells and cancer," *Science* 266:2011-2015 (1994).

Komeda et al., "Sensitive detection of circulating heptocellular carcinoma cells in peripheral venous load," *Cancer* 75:2214-2219 (1995).

Landgraf et al., "Direct analysis of polymerase chain reaction products using enzyme-linked immunasorbent assay techniques," *Analytical Biochmistry* 198:86-91 (1991).

Landgraf et al., "Quantitative analysis of polymerase chain reaction (PCR) products using primers labeled with biotin and a fluorescent dye," *Analytical Biochemistry* 193:231-235 (1991).

Larson et al., "Radioisotope Conjugates," *In: Biologic Therapy of Cancer* (DeVita, Hellman, Rosenberg, eds) J.B. Lippincott, Co., Philadelphia (1991) pp. 496-511.

Leon et al., "A Comparison of DNA and DNA-binding Protein Levels in Malignant Disease," *Europ J Cancer* 17:533-538 (1981).

Maruyama et al., "Detection of AMLi/ETO fusion transcript as a tool for diagnosing t(8;21) positive acute myelogenous leukemia," *Leukemia* 8:40-45 (1994).

Masella et al., "Characterization of Vesicles, Containing an Acylated Oligopeptide, Released by Human Colon Adenocarcinoma Cells," *FEBS Lett* 246:25-29 (1989).

McCabe et al., "Minimal Determinant Expressed by a Recombinant Viaccinia Virus Elicits Therapeutic Antitumor Cytolytic T Lumphocyte Responses," *Cancer Research* 55:1741-1747 (1995).

Miller et al., "Detection of minimal residual disease in acute promyelocytic leukemia by a reverse transcription polymerase chain reaction assay for the PML/RAR-alpha fusion mRNA," *Blood* 82:1689-1694 (1993).

Moore et al., "Design of PCR primers that detect only mRNA in the presence of DNA," *Nucleic Acids Research* 18:1921 (1991).

Mori, et al., "Detection of Cancer Micrometastases in Lymph Nodes by Reverse Transcriptase-Polymerase Chain Reaction," *Cancer Research* 55:3417-3420 (1995).

Mountford et al., "Proteolipid Identified by Magnetic Resonance Spectroscopy in Plasma of a Patient with Borderline Ovarian Tumor," *Lancet* i:829-834 (1987).

Nguyen, "Southern blot analysis of polymerase chain reaction products on acrylamide gels," *Bio Techniques* 7:238-240 (1989).

Ozcelik et al., "Low Levels of Expression of an Inhibitor of Cyclin-dependent Kinases (CIP1/WAF1) in Primary Breast Carcinomas with p53 Mutations," *Clinical Cancer Research* 1:907-912 (1995).

Patard et al., "Expression of MAGE genes in transitional-cell carcinomas of the urinary bladder," *mt J Cancer* 64:60-64 (1995).

Penno et al., "Expression of CD44 in human lung tumors," *Cancer Research* 54:1381-1387 (1994).

Peoples et al., "Breast and Ovarian Cancer-Specific Cytotoxic T Lymphocytes Recognize the same HER-2/Neu Derived Peptide," *Proc Natl Acad Sci USA* 92:432-436 (1995).

Pfleiderer et al., "Detection of tumor cells in peripheral blood and bone marrow from ewing tumor patients by RT-PCR," *Int J Cancer (Pred. Oncol)* 64:135-139 (1995).

Polushin et al., "Antisense Pro-Drugs: 5'-ester oligodeoxynucleotides," *Nucleic Acids Research* 22:5492-5496 (1994).

Rashtchian, "Amplification of RNA," *PCR Methods Applic* 4:S83-S91 (1994).

Reddi and Holland, "Elevated Serum Ribonuclease in Patients with Pancreatic Cancer," *Proc Nat Acad Sci USA* 73:2308-2310 (1976).

Rieber and Bacalao, "An 'external' RNA removable from mammalian cells by mild proteolysis," *Proc Natl Acad Sci USA* 71:4960-4964 (1974).

Roggenbuck et al., "Human Papillomavirus Type 18 E6 and E6, and E7 Protein Synthesis in Cell Free Translation Systems and Comparison of E6 and E7 in Vitro Translation Products to Proteins Immunoprecipitated from Human Epthelial Cells," *J Viral* 65:5068-72 (1991).

Rosenberg-Nicolson et al., "Nucleoprotein Complexes Released from Lymphoma Nuclei that Contain the abl Oncogene and RNA and DNA Polymerase and RNA Primase Activities," *J Cell Biochem* 50:43-52 (1992).

Rosi et al., "RNA-Lipid Complexes Released from the Plasma Membrane of Human Colon Carcinoma Cells," *Cancer Lett* 39:153-160 (1988).

Saiki et al., "Genetic analysis of amplified DNA with immobilized sequence-specific oligonucleotide probes," *Science* 233:1076-1078 (1989).

Sakakura et al., "Inhibition of gastric cancer cell proliferation by antisense oligonucleotides targeting the messenger RNA encoding proliferating cell nuclear antigen," *Br J Cancer* 70:1060-1066 (1994).

Schlom, "Antibodies in cancer therapy: basic principles of monaclanal antibodies," *In: Biologic Therapy of Cancer*, (DeVita, Hellman, Hellman, Rosenberg, eds) J.B. Lippincott, Co., Philadelphia (1991) pp. 464-481.

Shea et al., "Identification of the Human Prostate Carcinoma Onogene PTI-1 by Rapid Expression Cloning and Differential RNA Display," *Proc Natl Acad Sci USA* 92:6778-6782 (1995).

Skorski et al., "Suppression of philadelphial leukemia cell growth in mice by BORABL antisense oligodeoxynucleotide," *Proc Natl Aced Sci USA* 91:4504-4508 (1994).

Smith et al., "Detection of Melanoma Cells in Peripheral Blood by Means of Reverse Transcriptase and Polymerase Chain Reaction," *Lancet* 338:1227-1229 (1991).

Sooknanan et al., "Detection and direct sequence identification of BCR-ABL mRNA in Ph+ chronic myeloid leukemia," *Experimental Hematology* 21:1718-1724 (1993).

Stock et al., "Value of molecular monitoring during the treatment of chronic myeloid leukemia: A cancer and leukemia group B study," *J Olin Oncology* 15:26-36 (1997).

Stroun et al., "Neoplastic characteristics of the DNA found in the plasma of cancer patients," *Oncology* 46:318-322 (1989).

Taylor and Blak, "Shedding of Plasma Membrane Fragments. Neoplastic and Developmental Importance," *In: The Cell Surface in Development and Cancer, Develop Biol* 3:33-57 Editor: M.S. Steinberg. Plenum Press, New York, London (1985).

Urdea et al., "Branched DNA amplification multimers for the sensitive, direct detection of human hepatitis viruses," *Nucleic Acids Research Symposium Series* 24:197-200 (1991).

Vandamme et al., "Detection of HIV-1 RNA in plasma and serum samples using the NASBA amplification system compared to RNA-PCR," *J Virological Methods* 52:121-132 (1995).

Vitetta et al., "Immunatoxins," *In: Biologic Therapy of Cancer*(DeVita, Hellman, Rosenberg, eds) J.B. Lippincott, Co., Philadelphia (1991) pp. 482-495.

Wang et al., "Quantitation of mRNA by the polymerase chain reaction," *Proc Natl Acad Sci USA* 86:9717-9721 (1989).

Wieczorek et al., "Diagnostic and Prognostic Value of RNA-Proteolipid in Sera of Patients with Malignant Disorders Following Therapy; First Clinical Evaluation of a Novel Tumor Marker," *Cancer Research* 47:6407-6412 (1987).

Wieczorek et al., "Gensondentest Fur RNA-Proteolipid in Serumproben Bei Neoplasie," *Schweiz med Wschr* 119:1342-1343 (1989).

Wieczorek et al., "Isolation and Characterization of an RNA-Proteolipid Complex Associated with the Malignant State in Humans," *Proc Natl Acad Sci USA* 82:3455-3459 (1985).

Wiedmann et al., "Ligase chain reaction (LCR)—overview and applications," *POR Methods Applic* 3:551-564 (1994).

Yanuck et al., "A Mutant P53 Tumor Suppressor Protein is a Target f or Peptide-Induced 0DB' Cytotoxic T-Cells," *Cancer Research* 52:3257-3261 (1993).

Office Action, Non-Final Rejection mailed on Nov. 4, 1999 for U.S. Appl. No. 09/155,152.

Office Action, Non-Final Rejection mailed on Apr. 20, 2000 for U.S. Appl. No. 09/155,152.

Office Action, Final Rejection mailed on Oct. 25, 2000 for U.S. Appl. No. 09/155,152.

Office Action, Final Rejection mailed on Apr. 20, 2001 for U.S. Appl. No. 09/155,152.

Office Action, Non-Final Rejection mailed on Nov. 4, 1999 for U.S. Appl. No. 09/210,671.

Office Action, Non-Final Rejection mailed on Aug. 7, 2002 for U.S. Appl. No. 09/966,515.

Office Action, Non-Final Rejection mailed on Nov. 19, 2002 for U.S. Appl. No. 09/966,515.

Office Action, Non-Final Rejection mailed on Dec. 4, 2002 for U.S. Appl. No. 10/013,868.
Office Action, Final Rejection mailed on May 20, 2003 for U.S. Appl. No. 10/013,868.
Office Action, Non-Final Rejection mailed on Oct. 25, 2002 for U.S. Appl. No. 10/013,294.
Office Action, Non-Final Rejection mailed on Aug. 30, 2005 for U.S. Appl. No. 10/201,382.
Office Action, Final Rejection mailed on Mar. 15, 2006 for U.S. Appl. No. 10/201,382.
Office Action, Non-Final Rejection mailed on Jan. 10, 2007 for U.S. Appl. No. 10/201,382.
Office Action, Final Rejection mailed on Sep. 10, 2007 for U.S. Appl. No. 10/201,382.
Office Action, Non-Final Rejection mailed on Nov. 16, 2005 for U.S. Appl. No. 10/288,935.
Office Action, Final Rejection mailed on Jun. 12, 2006 for U.S. Appl. No. 10/288,935.
Office Action, Non-Final Rejection mailed on Feb. 23, 2007 for U.S. Appl. No. 10/288,935.
Office Action, Final Rejection mailed on Oct. 4, 2007 for U.S. Appl. No. 10/288,935.
Office Action, Non-Final Rejection mailed on Aug. 24, 2006 for U.S. Appl. No. 10/658,873.
Office Action, Final Rejection mailed on Apr. 9, 2007 for U.S. Appl. No. 10/658,873.
Office Action, Non-Final Rejection mailed on Jan. 28, 2008 for U.S. Appl. No. 10/658,873.
Office Action, Final Rejection mailed on Jul. 10, 2008 for U.S. Appl. No. 10/658,873.
Office Action, Non-Final Rejection mailed on Dec. 15, 2006 for U.S. Appl. No. 10/684,633.
Office Action, Final Rejection mailed on Jun. 21, 2007 for U.S. Appl. No. 10/684,633.
Office Action, Non-Final Rejection mailed on Jan. 28, 2008 for U.S. Appl. No. 10/684,633.
Office Action, Non-Final Rejection mailed on May 3, 2007 for U.S. Appl. No. 10/912,367.
Office Action, Final Rejection mailed on Aug. 10, 2007 for U.S. Appl. No. 10/912,367.
Office Action, Non-Final Rejection mailed on Feb. 6, 2008 for U.S. Appl. No. 10/912,367.
Office Action, Final Rejection mailed on Dec. 1, 2008 for U.S. Appl. No. 10/912,367.
Office Action, Non-Final Rejection mailed on Apr. 2, 2008 for U.S. Appl. No. 11/216,858.
Office Action, Final Rejection mailed on Nov. 14, 2008 for U.S. Appl. No. 11/216,858.
Office Action, Non-Final Rejection mailed on Oct. 2, 2008 for U.S. Appl. No. 11/346,590.
Office Action, Non-Final Rejection mailed on Nov. 13, 2008 for U.S. Appl. No. 11/357,399.
Office Action, Non-Final Rejection mailed on Sep. 22, 2008 for U.S. Appl. No. 11/364,842.
Office Action, Non-Final Rejection mailed on Sep. 10, 2008 for U.S. Appl. No. 11/421,260.
Office Action, Non-Final Rejection mailed on Jan. 8, 2009 for U.S. Appl. No. 11/416,470.
Office Action, Non-Final Rejection mailed on Oct. 8, 2008 for U.S. Appl. No. 11/416,788.
Serra et al. (2001), Neurological Sciences 22(2): 171-173.
Shen et al. (1995), Proc. Natl. Acad. Sci. U. S. A. 92: 6778-6782.
Shutack et al. (1968), J. Am. Osteopath. Assoc. 67(9): 1051-1053.
Stroun et al. (1978), Cancer Res. 38(10): 3546-3554.
Tamamiyagi et al. (1996), J. Dermatol. Sci. 11(2): 154-60.
Urdea et al. (1993), AIDS 7(suppl. 2): S11-S14.
Rohde et al. (2000), Clin. Cancer Res. 6: 4803-4809.
Keller et al. (1993), PCR Methods and Applications 3: 32-38.
Nolte et al. (1994), J. Clin. Microbiology 32: 519-520.
Schmidt et al. (1995), J. Med. Virology 47: 153-160.
Agliullina et al. (1988), Eksp. Onkol (USSR) 10(4), English abstract.
Schwarz et al. (1995), Res. Virol (Paris) 146(5), English abstract.
Kato et al. (1993), Hepatology 18(1), abstract.
Glick et al. (1994), Molecular biotechnology: Principles and applications of recombinant DNA, ASM Press: Washington DC. Table of Contents for Molecular Diagnostics (8) and Vaccines and Therapeutic Agents (9).
Persing et al (1993), Diagnostic molecular microbiology: Principles and applications, Amer. Soc. Microbiol. Washington DC, Table of Contents for Principles of Diagnostic Molecular Microbiology and Viral Pathogens.
Southall et al. (1990), Br. J. Cancer 61: 89-95.
Kopreski et al. (2001), Ann. N. Y. Acad. Sci 945: 172-178.
Yan-Sanders et al. (2002), Cancer Letters 183: 215-220.
Khimani et al. (2005), BioTechniques 38: 739-745.
Schrader et al. (2002), BMC Cancer 2: 32.
Fleischhacker et al. (2001), Ann. N. Y. Acad. Sci. 945: 179-188.
Burd et al. (1989), Proc. Natl. Acad. Sci. U. S. A. 86: 9788-9792.
Burchill et al. (1995), Br. J. Cancer 71: 278-281.
Lasheeb et al. (1997), Genitourinary Medicine 73(4): 303-305.
Mermin et al. (1991), J. Infectious Diseases 164(4): 769-772.
Kopreski et al. (2001), Clin. Chem. 47: 362, abstract 9.
Pelosi et al. (2006), Virchows Arch. 448: 7-15.
Tahara et al. (1999), Oncogene 18: 1561-1567.
Dasi et al. (2001), Lab. Investigation 81: 767-769.
Hasselmann et al. (2001), Oncol. Rep. 8: 115-118.
Ng et al. (2002), Clin. Chem. 48: 1212-1217.
Chen et al. (2000), Clin. Cancer Res. 6: 3823-3826.
Silva et al. (2001), Clin. Cancer Res. 7: 2821-2825.
Silva et al. (2001), Oncol. Rep. 8: 693-696.
Gal et al. (2001), Ann. N. Y. Acad. Sci. 945: 192-194.
Miura et al. (2003), Oncology 64: 430-434.
Wong et al. (2004), J. Clin. Pathol. 57: 766-768.
Ma et al. (2007), Haematologica 92: 170-175.
Arcari et al. (1984), Nucleic Acids Res. 12: 9179-9189.
Rykova et al. (2006), Ann. N. Y. Acad. Sci. 1075: 328-333.
Hernandez et al. (1999), Leukemia 13: 2087-2093.
Zhou et al. (1998), Clin. Cancer Res. 4: 1631-1640.
Zhou et al. (2001), Breast Cancer Research and Treatment 66: 217-224.
Press et al. (1990), Oncogene 5: 953-962.
Ng et al. (2003), Proc. Natl. Acad. Sci. U. S. A. 100: 4748-4753.
Ba Rey et al. (2002), Arch. Pathol. Lab. Med. 126: 574-576.
Gilmour et al. (2001), Cancer Res. 61: 2169-2716.
Reinhold et al. (2001), Clin. Chem. 47: 369, abstract 50.
Rajagopal et al. (1995), Int. J. Cancer 62: 661-667.
Dahiya et al. (1996), Urology 48: 963-970.
LeRiche et al. (1996), J. Clin. Endocrinol. Metab. 81: 656-662.
Pfeiffer et al. (1997), Int. J. Cancer 72: 581-586.
De Luca et al. (2000), Clin. Cancer Res. 6: 1439-1444.
Schlegel et al. (1994), Int. J. Cancer 56:72-77.
Worm et al. (1999), Hum. Pathol. 30: 222-227.
Pawlowski et al. (2000), Cancer Detect. Prev. 24: 212-223.
Walch et al. (2001), Lab. Invest. 81: 791-801.
Sarkar et al. (1993), Diagn. Mol. Pathol. 2: 210-218.
Gebhardt et al. (1998), Biochem. Biophys. Res. Comm. 247: 319-323.
Revillion et al. (1997), Clin. Chem. 43: 2114-2120.
Schneeberger et al. (1996), Anticancer Res. 16: 849-852.
Kraehn et al. (2001), Br. J. Cancer 84: 72-79.
Gamberi et al. (1998), Oncology 55: 556-563.
Sagawa et al. (2001), Cancer Letters 168: 45-50.
Christoph et al. (1999). Int. J. Cancer 84: 169-173.
Latil et al. (2000), Int. J. Cancer 89: 172-176.
Zhou et al. (1996), J. Biol. Chem. 271: 10760-10766.
Kozu et al. (1995), Genomics 25: 365-371.
Gocke et al. (2001), Clin. Chem. 47: 369, abstract 51.
Poon et al. (2001), Clin. Chem. 47: 363, abstract 11.
Urnovitz et al. (1999), Clin. Diag. Lab. Immunology 6: 330-335.
Zhao et al. (1994), Circulation 90: 677-685.
Dhillon et al. (2001), Exp. Neurol. 170: 140-148.
Fleischhacker et al. (2001), Clin. Chem. 47: 369 (Oral Presentation).
El-Hefnawy et al. (2004), Clin. Chem. 50(3): 564-573.
Tschentscher et al. (2000), Int. J. Clin. Lab. Res. 30(1): 13-15.
Missov et al. (1999), Clinica Chimica Acta 284: 175-185.
Sarko et al. (2002), J. Emerg. Med. 23(1): 57-65.

Jurlander et al. (2000), Eur. Heart J. 21: 382-289.
Rainer et al. (2003), Clin. Chem. 50(1): 206-208.
Townsend et al. (1995), J. Mol. Cell. Cardiol. 27: 2223-2236.
Mizuno et al. (2001), Blood 97(5): 1172-1179.
Meikl et al. (1998), Leukemia 12: 311-316.
Eads et al. (1999), Cancer Res. 59: 2302-2306.
Robertson et al. (1999), Nucleic Acids Res. 27(11): 2291-2298.
Fleischhacker and Schmidt (2007), Biochim. Biophys. Acta 1775: 181-232.
Lion et al. (1995), Leukemia 9: 1353-1360.
El-Deiry, et al. (1991), Proc. Natl. Acad. Sci. U. S. A. 88: 3470-3474.
Lo et al. (1999), Clin. Chem. 45(8): 1292-1294.
Chen et al. (1999), Int. J. Cancer 83: 10-14.
Saito et al. (2001), Hepatology 33: 561-568.
Moreno et al. (1992), Cancer Res. 52: 5110-5112.
Wieczorek et al. (1989), Schweiz med Wschr 119: 1342-1343.
Wieczorek et al. (1985), Proc. Natl. Acad. Sci. U. S. A. 82: 3455-3459.
Edmands et al. (1994), PCR Methods. Applic. 3: 317-319.
Reddi et al., "Elevated serum ribonuclease in patients with pancreatic cancer," Proc. Natl. Acad. Sci. 73(7)2308-10 (Jul. 10, 1976).
Spiegelman et al., (1969) The Harvey Lectures No. 64, pp. 1-67.
Kopreski et al., "Detection of tumor messenger RNA in the serum of patients with malignant melanoma." Clinical Cancer Research 5:1961-65 (Aug. 1999) 5:1961-65.
Leitzel et a., "Detection of cancer cells in peripheral blood of breast cancer patients using reverse transcription-polymerase chain reaction for epidermal growth factor receptor." Clincal Cancer Research 4:3037-43 (Dec. 1998).
Tamamiyagi et al., "Quantitative analysis of ferrochelatase mRNA in blood cells of erythropoietic protoprophyria patients." Journal of Dermatological Science 11(2) 154-60 (Feb. 1996).
Garbarz et al., "Spectrin Beta-Tandil A Novel Shortened Beta-Chain Variant Associated with Hereditary Elliptocytosis is due to a Deletional Frameshift Mutation in the Beta Spectrin Gene," Blood 80(4)1066-73 (1992).
Monteyne et al., "Expression of costimutatory molecules and cytokines in CSF and peripheral Blood mononuclear cells from multiple sclerosis patients" Acta Neurological Belgica 1(99):11-20 (Mar. 1999).
Serra et al., "Multiple sclerosis and multiple sclerosis-associated retrovirus in Sardinia" Neurological Sciences 22(2) 171-73 (Apr. 2001).
Kopreski et al., "Cellular-versus extracellular-based assays. Comparing utility in DNA and RNA molecular marker assessment" Annals of New York Academy of Sciences 906:124-8 (Apr. 2000).
Messner et al., "Expression of messenger RNA of the cardiac isoforms of troponin T and I in myopathic skeletal muscle" American Journal of Clinical Pathology 114(4)544-49(Oct. 2000).
Kamm et al., "Nucleic-Acid Concentrations in Normal Human Plasma" Clinical Chemistry 18(6)519-22 (1972).
Shutack et al., "A Study of the RNA levels of normal blood serum" The Journal of the American Osteopathic Association 67(9)1051-53 (May 1968).
Guin et al., "Electrophoretic Characterization of Plasma RNA" Biochemical Medicine 13(3)224-30 (1975).
Stroun et al., "Presence of RNA in the nucleoprotein complex spontaneously released by human lymphocytes and frog auricles in culture" Cancer Research 38(10)3546-3554 (Oct. 1978).
Allouche et al., "Expression of basic fibroblast growth factor (bFGF) and FGF-receptors in human leukemic cells" Leukemia:Official Journal of the Leukemia Society of America, Leukemia Research Fund 9(1)77-86 (Jan. 1995).
Ricchiuti et al., "Expression of cardiac troponin T mRNA in skeletal muscle from patients with end stage renal disease and muscular dystrophy" Clinical Chemistry 45(6)A144-A145 (Jun. 1999).
Ricchiuti et al., "RNA expression of cardiac troponin T isoforms in diseased human skeletal muscle" Clinical Chemistry 45(12)2129-35 (Dec. 1999).
Ricchiuti et al., "Cardia troponin I and T alterations in hearts with severe left ventricular remodeling" Clinical Chemistry 43(6)990-95 (1997).
Rosenzweig et al., "Preclinical Diagnosis of Familial Hypertrophic Cardiomyopathy by Genetic Analysis of Blood Lymphocytes" New England Journ of Med 325(25)1753-60 (Nov. 19, 1981).
Spiegelman et al., "The Development and Use of and Extracellular RNA Replicating System" The Harvey Lectures No. 64 pp. 1-67 (1969).
Bairey et al. (2002), "Lack of HER-2/neu expression in Hodgkin and non-Hodgkin lymphoma," Arch. Pathol. Lab. Med. 126:574-576.
Durie et al. (2000), "RT-PCR amplicons in the plasma of multiple myeioma patients—clinical relevance and molecular pathology," Acta Oncol. 39 789-796.
Lee et al. (1996), "Limited up-regulation of DNA methyltransferase in human colon cancer reflecting increased cell proliferation," Proc. Natl. Acad. Aci. U. S. A. 93: 10366-10370.
Begum et al. (1996), "Loss of hIRH mRNA expression from premalignant adenomas and malignant cell lines." Biochemical and Biophysical Research Communications 229: 864-8.
Carpenter et al. (2006), "The roles of heterogenous nuclear ribonucleoproteins in tumour development and progression." Biochimica et Biophysica Acta 1765: 85-100.
Definition of "erbB" from Wikipedia, accessed on Sep. 13, 2009.
Definition of "extracellular" from Wikipedia, accessed on May 15, 2009.
Definition of "intracellular" from Wikipedia, accessed on May 15, 2009.
Definition of "Myc" from Wikipedia, accessed on Sep. 15, 2008.
Definitions of "oncogene" from Google search, accessed on Aug. 3, 2007.
Definition of "precancerous (premalignant) condition" from Wikipedia, accessed on Apr. 20, 2009.
Kolquist et al. (1998), "Expression of TERT in early premalignant lesions and a subset of cells in normal tissues." Nature Genetics 19: 182-6.
Lledo et al. (2004), "Real time quantification in plasma of human telomerase reverse transcriptase (hTERT) mRNA in 10 patients with colorectal cancer." Colorectal Disease 6(4): 236-42.
Ng et al. (2004), "Evaluation of human chorionic gonadotropin beta-subunit mRNA concentrations in maternal serum 11 in aneuploid pregnancies: a feasibility study." Clinical Chemistry 50: 1055-7.
"Principle of cycling probe technology," description from Takara Bio Inc. website, printed May 1, 2009.
Shibuta et al. (2002), "Regional expression of CXCL 12/CXCR4 in liver and hepatocellular carcinoma and cell-cycle variation during in vitro differentiation." Jpn. J. Cancer Res. 93: 789-97.
Steketee et al. (1997), "Early detection of perinatal human immunodeficiency virus (HIV) type 1 infection using HIV RNA amplification and detection. New York City Perinatal HIV Transmission Collaborative Study." J. Infect. Dis. 175(3):707-11.
Sueoka et al. (2005), "Detection of plasma hnRNP B1 mRNA, a new cancer biomarker, in lung cancer patients by quantitative real-time polymerase chain reaction." Lung Cancer 48: 77-83.
Tsui et al. (2002), "Stability of endogenous and added RNA in blood specimens, serlim, and plasma," Clin. Chem. 46: 16 1647-1653.
Wagner et al. (1995), "Patterns of p53, erbB-2, and EGF-r expression in premalignant lesions of the urinary bladder." Human Pathology 26: 970-8.
Wong et al. (2004), "Quantification of plasma beta-catenin mRNA in colorectal cancer and adenoma patients." Clinical Cancer Research 10: 1613-7.
Wong et al. (2006), "Plasma RNA integrity analysis: methodology and validation," Ann. N. Y. Acad. Sci. 1075: 174-178.
Zhou et al. (2008), "Circulating RNA as a novel tumor marker: an in vitro study of the origins and characteristics of extracellular RNA," Cancer Letters 259: 50-60.

* cited by examiner

COMPARATIVE ANALYSIS OF EXTRACELLULAR RNA SPECIES

This application is a continuation-in-part of U.S. Ser. No. 10/658,873, filed Sep. 5, 2003, which is a continuation-in-part of U.S. Ser. No. 10/013,868, filed Oct. 30, 2001, now U.S. Pat. No. 6,939,671 B2, issued Sep. 6, 2005, which is a continuation of U.S. patent application, Ser. No. 09/155,152, filed Sep. 22, 1998, now U.S. Pat. No. 6,329,179 B1, which is a U.S. national phase application filed pursuant to provisions of 35 U.S.C. 371 of International Application Serial No. PCT/US97/03479, filed Mar. 14, 1997, which claims the benefit of the filing date of Provisional U.S. patent application, Ser. No. 60/014,730, filed Mar. 26, 1996, the entire disclosure of each of which is hereby incorporated by reference.

BACKGROUND OF THE INVENTION

Ribonucleic acid (RNA) plays an essential role in the translation of the genetic code to produce proteins necessary for cellular function, both in normal cells and neoplastic or diseased cells. In particular, RNA including transfer RNA, messenger RNA or messenger-like RNA, and ribosomal RNA carry and translate the genetic code to sites of protein production. Further, double-stranded RNA and species therefrom, including small inhibitory RNA or siRNA, and micro RNA or miRNA, play an important role in silencing genetic expression. Other RNA species are found within ribonucleoproteins. For example, telomerase RNA is a critical component of telomerase, an important ribonucleoprotein highly expressed in most cancers. The pathogenesis and regulation of cancer is thus dependent upon RNA-mediated translation and/or inhibitory control of specific genetic code, said genetic code often reflecting mutational events or other alterations within deoxyribonucleic acid (DNA), including epigentic alterations such as hypermethylation, microsatellite alterations, loss of heterozygosity, translocations, deletions, and point mutations. Further, other RNA species and their associated proteins, although not necessarily being directly involved in neoplastic pathogenesis or regulation, may provide recognizable characterization of neoplasia or disease by being inappropriately expressed or elevated. Such overexpression of RNA thus can delineate cancer or other disease. Recognition of the presence or overexpression of specific RNA, including both coding and non-coding RNA, can enable identification, detection, inference, monitoring, or evaluation of any neoplasm, whether benign, malignant, or premalignant, in humans and animals.

U.S. Pat. No. 6,329,179 B1, incorporated herein in its entirety, teaches that both tumor-associated and non-tumor associated RNA are detectable in plasma and serum. Total RNA, to be understood in the cancer patient to comprise both tumor-associated and non-tumor-associated RNA and further being heterogeneous RNA, can be extracted from plasma or serum, the RNA of interest or its cDNA is amplified qualitatively or quantitatively, and the amplified product of an RNA or cDNA species of interest detected. Subsequent art supports these teachings by demonstrating that extracellular RNA of various RNA species are detectable in bodily fluids, for example in co-owned U.S. Pat. No. 6,607,898; Kopreski et al., 1999, *Clin. Cancer Res.* 5: 1961-1965; Dasi et al., 2001, *Lab. Investigation* 81: 767-769; Hasselmann et al., 2001, *Oncol. Rep.* 8: 115-118; Ng et al., 2002, *Clin. Chem.* 48: 1212-1217; Chen et al., 2000, *Clin. Cancer Res.* 6: 3823-3826; Silva et al., 2001, *Clin. Cancer Res.* 7: 2821-2825; Silva et al., 2001, *Oncol. Rep.* 8: 693-696; Gal et al., 2001, *Ann. NY Acad. Sci.* 945: 192-194; Durie et al., 2000, *Acta Oncol.* 39: 789-796; Fleischhacker et al., 2001, *Ann. NY Acad. Sci.* 945: 179-188; Miura et al., 2003, *Oncology* 64: 430-434; Kopreski et al., 2001, *Ann. NY Acad. Sci.* 945: 172-178; and Wong et al., *J. Clin. Pathol.* 2004, 57: 766-768, said references incorporated herein in their entirety. Detection of tumor-associated RNA in plasma or serum thus provides a method for detecting, diagnosing, inferring, or monitoring cancer or premalignancy in a human or animal.

Neoplasia is characterized by varying degrees of invasiveness, metastatic potential, and resistance or responsiveness to particular therapies. Furthermore, these characteristics for a given neoplasia may change over time, for example by becoming progressively more malignant, invasive, metastatic, heterogeneous, undifferentiated, or treatment-resistant. Phenotypic changes often reflect underlying molecular changes. In particular, the relative ratio of particular RNA species, including coding and non-coding species, to each other, and/or to DNA, and/or to proteins can determine the characteristics of the neoplasia.

Comparative analysis of extracellular RNA species to each other, and/or to extracellular DNA, and/or to extracellular protein, would thus be useful as a method for detecting, diagnosing, inferring, characterizing, or monitoring cancer or premalignancy in a human or animal. Said comparative analysis further enables the selection and monitoring of treatment. To optimize the reliability and reproducibility of such comparative analysis, there is a need in the art for methods that maintain the stability of extracellular plasma RNA species and their concentrations and relative ratios within a plasma or serum or bodily fluid specimen over time. Although extracellular RNA is generally protected from the degrading effects of plasma RNase by being protected within phospholipid-encapsulated particles such as apoptotic bodies, a variable disruption of the particles or apoptotic bodies may occur over time or consequent to mechanical manipulations such as freeze-thawing or centrifugation, leading to variable rates of degradation of the extracellular RNA through its exposure to nucleases. The present invention provides methods to enhance the intra-specimen stability and reproducibility of the ratio between two or more RNA species in a plasma or serum or bodily fluid specimen, and kits thereof.

Thus, there is a need in the art for methods of comparing the amount or concentration or relative ratio of two or more plasma or serum RNA species or fragments thereof to permit diagnosis, detection, inference, evaluation, or monitoring of neoplastic disease in a human or animal. It is to be explicitly understood that said comparison of two or more RNA species may include comparison of non-mutated tumor RNA to tumor RNA; tumor RNA to non-mutated non-tumor RNA; coding RNA to coding RNA; coding RNA to non-coding RNA; and non-coding RNA to non-coding RNA; or any combination thereof. There is a need in the art for methods of enhancing the reliability and reproducibility of said comparisons.

Furthermore, there is a need for methods of comparing the amount or concentration or ratio of one or more extracellular RNA species to the amount or concentration of total RNA or extracellular DNA or protein present in the plasma, serum, or bodily fluid of a human or animal for the diagnosing, detecting, inferring, evaluating, or monitoring cancer and other neoplastic diseases in the human or animal.

SUMMARY OF THE INVENTION

The invention provides methods for diagnosing, detecting, inferring, evaluating, or monitoring cancer or other neoplastic disease in a human or animal by determining the amount, concentration, ratio, or other quantitative or comparative assessment between two or more extracellular RNA species in plasma or serum or other bodily fluid from a human or animal, where in the preferred embodiment the extracellular RNA species have been stabilized from degradation by nucleases. The invention further provides methods for comparing one or more specific extracellular RNA species in plasma or serum or bodily fluid to another within said specimen, or to extracellular total RNA, extracellular DNA, or extracellular protein within said plasma, serum, or bodily fluid specimen. The methods provided by the invention comprise qualitative or quantitative determination of the amount or concentration or ratio between at least two extracellular RNA species in a bodily fluid specimen by any of means known to the art, including but not limited to nucleic acid amplification, signal amplification, spectroscopy including mass spectroscopy, and hybridization methods using detectably-labeled probes. The methods provided by the invention further comprise qualitative or quantitative determination of a least one extracellular RNA species within a bodily fluid specimen to one or more of the following group within said specimen: total extracellular RNA, total extracellular DNA, one or more extracellular DNA species, one or more extracellular proteins. It is to be understood that within this specification, RNA species refers to RNA selected from one or more of the group comprising messenger RNA, inhibitory RNA, coding RNA, non-coding RNA, RNA having a sequence complimentary to a mutated or altered DNA, RNA having a sequence complimentary to non-mutated DNA, and ribonucleoprotein RNA.

According to a first aspect of the present invention, there is provided methods for detecting, diagnosing, inferring, evaluating or monitoring disease, particularly cancer or neoplastic disease in a human or animal, the method comprising the steps of combining plasma, serum or bodily fluid with an agent that protects or stabilizes RNA from degradation by RNase (hereafter referred to as stabilizing agent); thereafter extracting total extracellular RNA from plasma, serum or other bodily fluid specimen of a human or animal, determining quantitatively or qualitatively the amount or concentration of at least two extracellular RNA species from a fraction of said plasma, serum or other bodily fluid, wherein comparison of said RNA species thereby detects, diagnoses, infers, or monitors or enables evaluation of a cancer or neoplastic disease in a human or animal. In a particularly preferred embodiment, at least two of the RNA species are tumor-associated RNA, and cancer or neoplastic disease is detected, diagnosed or inferred or evaluated when the amount or concentration of at least one RNA species from the plasma, serum or bodily fluid is greater than the amount or concentration of another RNA species from the plasma, serum, or bodily fluid.

In another preferred embodiment, a cancer or neoplastic disease is detected, diagnosed or inferred or evaluated when at least two of the RNA species are detected in the plasma, serum, or bodily fluid of a human or animal.

In the preferred embodiment of the invention, the stabilizing agent is a RNase inhibitor or a RNase inactivator.

In another preferred embodiment of the invention, the stabilizer agent hybridizes to the RNA species.

In another preferred embodiment of the invention, the stabilizer agent is a protein that binds to the RNA species in a manner that stabilizes the RNA species against degradation by RNase.

In another preferred embodiment of the invention, the stabilizer agent is one that stabilizes a phospholipid membrane, thereby stabilizing the particle or apoptotic body encapsulating extracellular RNA in plasma, serum, or bodily fluid.

In another preferred embodiment of the invention, the stabilizer agent is one that promotes aggregation of particles or apoptotic bodies encapsulating extracellular RNA in plasma, serum, or bodily fluid, thereby protecting from RNase. In one aspect of this embodiment the stabilizing agent is a coated bead or particle. In another aspect of this embodiment, the stabilizing agent is coated solid surface.

According to another aspect of the present invention, there is provided methods for detecting, diagnosing, inferring, evaluating or monitoring disease, particularly cancer or neoplastic disease in a human or animal, the method comprising the steps of combining plasma, serum or bodily fluid with a stabilizing agent, extracting total extracellular RNA from plasma or serum or other bodily fluid specimen of the human or animal (test specimen), determining quantitatively or qualitatively the amount or concentration of one or a plurality of extracellular RNA species from a fraction of said test specimen, and comparing said amount or concentration of one or a plurality of extracellular RNA species obtained from the fraction of said specimen to the amount or concentration of one or a plurality of corresponding extracellular RNA species in reference group specimen. In one aspect said comparison to the reference group provides either a numerical or positive/negative assessment of each extracellular RNA species within the test specimen compared to the reference specimen, and thereafter comparison of the numerical or positive/negative values thereby ascribed to each RNA species from the test specimen to values of other RNA species within the test specimen is made, wherein said comparison or patterns determined thereby detects, diagnoses, infers, or monitors a cancer or neoplastic disease in a human or animal. In preferred embodiments, the reference group is a human or human population of individuals without cancer. In alternative preferred embodiments, the reference group is a human or human population of individuals with cancer.

According to another aspect of the present invention, there are provided methods for detecting, diagnosing, inferring, or monitoring cancer or neoplastic disease in a human or animal, the method comprising the steps of obtaining a plasma or serum specimen from the human or animal, combining the plasma or serum specimen with a stabilizing agent, determining directly on a portion of said specimen the amount or concentration of total extracellular RNA or of one or more RNA species within a portion of the plasma or serum specimen, comparing said amount or concentration to that of a reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of total extracellular RNA in the fraction of the specimen is greater than the amount or concentration of total extracellular RNA found in the reference group, or when one or more RNA species in the fraction of the specimen is greater than the amount or concentration of said species found in the reference group. In alternative preferred embodiments, the reference group is a human or human population of individuals with cancer, and cancer or neoplastic disease is detected, diagnosed or inferred when the amount or concentration of total extracellular RNA or one or more RNA species in the fraction of the specimen is not significantly less than the amount or concentration of total extracellular RNA found in the reference group. In an alternative preferred embodiment, the amount or concentration of one or more RNA species may be less than that of the reference group, whereby cancer or neoplastic disease is thereby detected, diagnosed, inferred, evaluated, or characterized. In one aspect of this embodiment, an extracellular messenger RNA is less than that of a reference group and an extracellular inhibitory RNA is greater than that of a reference group.

In another preferred embodiment, the invention provides methods for detecting, diagnosing, inferring, characterizing, evaluating, or monitoring cancer or neoplastic disease in a human or animal, the method comprising the steps of obtaining a plasma or serum specimen from the human or animal, combining the plasma or serum specimen with a stabilizing agent, determining directly on a portion of said specimen the amount or concentration of one or a plurality of extracellular RNA species in a portion of the plasma or serum specimen, comparing said amount or concentration to that of a reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of one or a plurality of extracellular RNA species is the fraction of the specimen in greater than the amount or concentration of one or a plurality of extracellular RNA species found in the reference group. In alternative preferred embodiments, the reference group is a human or human population of individuals with cancer, and cancer or neoplastic disease is detected, diagnosed or inferred when the amount or concentration of one or a plurality of extracellular RNA species in the fraction of the specimen is not significantly less than the amount or concentration of one or a plurality of extracellular RNA species found in the reference group.

In a preferred embodiment of the inventive methods, the bodily fluid is blood, plasma, serum, urine, effusions including pleural effusions, ascitic fluid, saliva, cerebrospinal fluid, gastrointestinal secretions, bronchial secretions including sputum, cervical secretions, or breast secretions. In a particularly preferred embodiment, the bodily fluid is plasma or serum.

In preferred embodiments of the inventive methods, the amount of total extracellular RNA, or one or a plurality of extracellular RNA species, is determined quantitatively or qualitatively using a method that is nucleic acid amplification, signal amplification, spectroscopy including mass spectroscopy, or hybridization, preferably to a detectably-labeled probe.

In preferred embodiments of the inventive methods, RNA is extracted from blood, plasma, serum, or other bodily fluid using an extraction method that is a gelatin extraction method; a silica, glass bead, or diatom extraction method; guanidinium thiocyanate acid-phenol based extraction methods; guanidinium thiocyanate acid based extraction methods; phenol-chloroform based extraction methods; by centrifugation through a cesium chloride or similar gradient; or using commercially-available RNA extraction methods, most preferably as provided in a kit comprising instructions from the kit manufacturer.

In preferred embodiments of the invention, RNA extracted from plasma, serum, or other bodily fluid is reverse transcribed to cDNA prior to detection or amplification and detection. In these embodiments, the amount or concentration of RNA is determined by qualitative or quantitative analysis of cDNA or amplified cDNA product.

In preferred embodiments of the invention, extracted RNA or the corresponding cDNA is amplified qualitatively or quantitatively to determine the amount or concentration of a RNA species, using an amplification method that is, for example, polymerase chain reaction, or reverse transcriptase polymerase chain reaction; ligase chain reaction; DNA or RNA signal amplification; amplifiable RNA reporter methods; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of amplified RNA or cDNA product is performed using a detection method that is, for example, gel electrophoresis; enzyme-linked immunosorbent assay (ELISA), including embodiments comprising biotinylated or otherwise modified amplification primers; hybridization using a specific, detectably-labeled probe, for example, a fluorescent-, radioisotope-, or chromogenically-labeled probe; Southern blot analysis; Northern blot analysis; electrochemiluminescence; reverse dot blot detection; high-performance liquid chromatography; and variations thereof.

The methods of the invention particularly provide methods for identifying humans at risk for developing a disease, particularly cancer or other neoplastic disease, or who have a malignancy or premalignancy. The methods of the invention thus provide methods for identifying humans having a malignancy such as breast, ovarian, lung, cervical, colorectal, gastric, pancreatic, bladder, endometrial, brain, kidney, or esophageal cancers, leukemias, lymphomas, melanoma, or sarcomas; and premalignancies including but not limited to colorectal adenoma, cervical dysplasia, cervical intraepithelial neoplasia (CIN), bronchial dysplasia, atypical hyperplasia of the breast, ductal carcinoma in-situ, atypical endometrial hyperplasia, and Barrett's esophagus.

The invention thus permits the presence of cancerous (malignant) or pre-cancerous (premalignant) cells within a human or animal to be detected or inferred by determining an amount or concentration of RNA in the plasma, serum, or other bodily fluid of said human or animal that exceeds the amount or concentration normally present in the plasma, serum, or other bodily fluid of a human or animal without cancer or pre-malignancy.

The invention also permits the existence of a disease within a human or animal to be detected or inferred by determining an amount or concentration of RNA in the plasma, serum, or other bodily fluid of said human or animal that exceeds the amount or concentration normally present in the plasma, serum, or other bodily fluid of a healthy human or animal.

An advantageous application of this invention is to identify humans or animals with disease.

It is a particularly advantageous application of this invention to identify humans or animals having cancer.

Another advantageous application of this invention is to identify humans or animals having risk for developing cancer.

Another advantageous application of this invention is to identify humans or animals having a premalignant disease.

Another advantageous application of this invention is for monitoring cancer, including response to cancer therapies, including surgery, biotherapy, hormonal therapy, anti-sense therapy, monoclonal antibody therapy, chemotherapy, vaccines, anti-angiogenic therapy, cryotherapy, radiation therapy, and therapies based upon or directed at inhibitory RNA or regulatory RNA, including siRNA and miRNA.

Another advantageous application of this invention is selecting humans or animals for cancer therapies, including surgery, biotherapy, hormonal therapy, anti-sense therapy, monoclonal antibody therapy, chemotherapy, vaccines, anti-angiogenic therapy, cryotherapy, radiation therapy, and therapies based upon or directed at inhibitory RNA or regulatory RNA, including siRNA and miRNA.

Another advantageous application of this invention is to provide a marker as a guide to whether adequate therapeutic effect has been achieved, or whether additional or more advanced therapy is required, and to assess prognosis in a patient.

Another advantageous application of this invention is to provide an indicator of a relapsed cancer following therapy, or impending relapse, or treatment failure.

Another advantageous application of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination, and physical examination.

The invention further provides kits that provide stabilizing agent for use in combination with plasma, serum, or bodily fluid to stabilize extracellular RNA within said plasma, serum, or bodily fluid.

The invention also provides diagnostic kits enabling quantitative or qualitative assessment of total RNA or specific RNA species in plasma or serum, wherein a reference range for normal values or cancer values is provided to enable identification or selection of a human or animal with or at risk for cancer.

Specific preferred embodiments of the present invention will become evident from the following more detailed description of certain preferred embodiments and the claims.

DETAILED DESCRIPTION OF THE INVENTION

This invention relates to methods for detecting, diagnosing, inferring, or monitoring cancer or neoplastic disease in a human or animal by stabilizing the extracellular RNA in plasma, serum, or bodily fluid, and thereafter assessing the amount or concentration of RNA in said plasma, serum, or other bodily fluid of the human or animal, and comparing the amount or concentration of one or more RNA species in said plasma, serum, or bodily fluid obtained from the human or animal with another, or with the amount or concentration of RNA found in bodily fluid from a reference individual, group or population of known disease status. In particular, the invention provides methods for detecting, inferring or monitoring the presence of cancerous or precancerous cells in a human or animal, whether from a non-hematologic neoplasm (i.e., a solid-tumor) or from a hematologic malignancy (such as leukemia, lymphoma, myeloma, etc.). The methods of the invention in the first step stabilize the extracellular RNA in plasma, serum or bodily fluid by combining plasma, serum, or bodily fluid with an agent that protects or stabilizes RNA from degradation by RNase, herein referred to as stabilizing agent, and thereafter in the next step or steps determine an amount, concentration or other quantitative or comparative assessment of RNA from a bodily fluid specimen obtained from a human or animal, wherein the RNA can be either total extracellular RNA, or one or a plurality of specific RNA species or multiple specific RNA species. RNA species may be either tumor-related RNA or non-tumor related RNA. Total extracellular RNA will be recognized as comprising both tumor-related and non-tumor-related RNA when obtained from a patient with cancer or other neoplastic disease. In preferred embodiments, the bodily fluid is blood, plasma, serum, urine, effusions including pleural effusions, ascitic fluid, saliva, cerebrospinal fluid, gastrointestinal secretions, bronchial secretions including sputum, cervical secretions, or breast secretions. Plasma and serum are particularly preferred bodily fluids, but any bodily fluid a portion of which comprises extracellular RNA, and particularly tumor-associated extracellular RNA is useful in the practice of the methods of this invention.

As used herein, the terms "tumor-associated," "disease-associated", "disease-related," "tumor-related" and "non-tumor-related" are intended to encompass particular RNA species, as well as total extracellular RNA. It will be understood that certain RNA species, such as oncogenic RAS, p53, and other RNA species, are recognized in the art as being associated with the existence of cells comprising a disease state, particularly neoplastic disease, malignancy or premalignancy. RNA species are "tumor-associated", "disease-associated," "disease-related," "tumor-related" when their presence as a component of total extracellular RNA is indicative of the existence of a disease, particularly a neoplastic disease. "Non-tumor-related" RNA species, on the other hand, comprise RNA species component(s) present in healthy individuals; but it is recognized that such species may also be present in individuals bearing disease-associated, disease-related, or tumor-related extracellular RNA species as well. It will be recognized that in certain embodiments of the methods of this invention, detecting a lack of expression of an RNA species comprising non-tumor-related RNA may further indicate the existence of disease in said human or animal.

As used herein, the term "RNA species" refers to RNA selected from one or more of the group comprising messenger RNA, inhibitory RNA, coding RNA, non-coding RNA, RNA having a sequence complimentary to a mutated or altered DNA, RNA having a sequence complimentary to non-mutated DNA, and ribonucleoprotein RNA. It is understood herein that RNA species may further be disease-associated, tumor-associated, disease-related, tumor-related, and non-tumor-related.

Qualitative or quantitative comparison of the amount or concentration of a RNA species from said human or animal bodily fluid specimen is made in comparison to another RNA species from said specimen, or to total RNA, extracellular DNA, or extracellular protein from said specimen, or to a standard from a reference individual, group, or population. Said assessment is made on the basis of a previously-determined reference set of values for said individual, group or population, or alternatively upon a newly determined reference set of values for the individual, group, or population. Comparison to the reference individual, group, or population thereby enables determination of the likelihood that the subject human or animal has a disease, particularly cancer or neoplastic disease such as premalignancy, wherein if the amount or concentration (or similar comparative RNA indicator) of total extracellular RNA or of one or a plurality of specific RNA species thereof from the bodily fluid of the subject human or animal is demonstrated to be greater than the amount or concentration (or similar comparative indicator) present in individuals, groups, or populations without disease, particularly cancer or neoplastic disease, then a disease, particularly cancer or an increased risk of cancer (for example, due to the existence of a premalignancy) will be inferred in the human or animal subject. Similarly, if the amount or concentration of total extracellular RNA, or of one or a plurality of specific RNA species thereof in the bodily fluid of the subject is within the range of a group or population with a disease, particularly cancer or neoplastic disease such as a premalignancy, then a disease, particularly cancer or an increased risk of cancer (for example, due to the existence of a premalignancy) will be inferred in the human or animal subject. If the amount or concentration of total extracellular RNA, or of one or a plurality of specific RNA species thereof in the bodily fluid of the subject is less than the range for patients with cancer, or within the range of the healthy population, then the risk of disease, particularly cancer or an increased risk of cancer (for example, due to the existence of a premalignancy) will be less. It will be recognized that the limits of the reference range values may be set in a manner that determines a sensitivity or specificity or positive predictive value or negative predictive value for the assay, or otherwise provides the probability of the assay correctly identifying a subject with cancer or neoplasm. Thus, in this manner the reference range for a group or population can be defined that increases the sensitivity or specificity of the assay.

It will also be recognized that lower concentrations of some extracellular RNA species relative to the reference group may be indicative of higher risk of malignancy.

It is to be recognized that a variety of individuals, groups, or populations will provide suitable reference values that enable discrimination of abnormal (disease-, and more particularly cancer-, related) and normal amounts or concentrations of total extracellular RNA, or of one or a plurality of specific RNA species thereof in the bodily fluid of the subject. Appropriate reference individuals, groups, or populations include but is not limited to: a healthy human or animal, more specifically a human or animal population without neoplastic disease (cancer or premalignancy) or a human or animal population without cancer; a human or animal population with a disease, more specifically a human or animal population with neoplastic disease (cancer or premalignancy) or a human or animal population with cancer; a previously-isolated bodily fluid specimen from the human or animal under evaluation corresponding to a known disease or health state. In addition, it will be recognized that certain defined groups or populations will provide useful reference values to assess probability of disease, particularly cancer or premalignancy, in a subject, including but not limited to: groups and populations defined by gender and the presence or absence of disease, particularly cancer or premalignancy; groups and populations defined by race or ethnicity and presence or absence of disease, particularly cancer or premalignancy; groups and populations defined by non-neoplastic diseases; groups and populations defined by specific tumor types; groups and populations defined by stage or extent of cancer of a particular type; groups and populations defined by certain environmental or occupational risks for cancer, such as smokers or workers occupationally exposed to carcinogens; and groups and populations defined by genetic or family risk for cancer. It is to be understood that the comparative assessment of the subject's extracellular RNA species of interest, or the subject's total extracellular RNA in a bodily fluid such as blood plasma or serum to reference groups and populations may be made by either non-statistical or statistical analysis, as is known to the art.

In particularly preferred embodiments of the invention, one or more RNA species present in plasma, serum, or non-cellular fraction of a bodily fluid of a human or animal is compared to one or more other RNA species within said plasma, serum, or non-cellular fraction of a bodily fluid, whereby comparative assessment of said RNA species is made by either non-statistical or statistical analysis, as known in the art. Comparative analysis of two or more extracellular RNA species in plasma, serum, or other bodily fluid thereby provides methods for detecting, inferring, characterizing, evaluating, or monitoring cancer or premalignancy. In one preferred aspect of this embodiment, the invention in the first step stabilizes the extracellular RNA in plasma, serum, or bodily fluid by combining RNA plasma, serum, or bodily fluid with an agent that protects or stabilizes RNA from degradation by RNase, herein referred to as stabilizing agent, and thereafter in the next step or steps is determined an amount, concentration, or other quantitative or comparative assessment of the RNA species of interest. Comparative assessment may be accomplished by extracting total RNA from the plasma, serum, or bodily fluid; amplifying or signal amplifying either sequentially or concurrently and in a qualitative or quantitative fashion the RNA species of interest, or cDNA derived therefrom, comprising a fraction of the extracted RNA; detecting the amplified products or amplified signal of the RNA species or cDNA derived therefrom; whereby detection, diagnosis, evaluation, characterization, or monitoring of cancer or premalignancy is thereby accomplished.

In another aspect of the preferred embodiment, comparative analysis of two or more extracellular RNA species from plasma, serum, or bodily fluid is accomplished without the step of providing the stabilizing agent to plasma, serum, or bodily fluid. In this aspect of the preferred embodiment, total RNA is extracted from plasma, serum, or bodily fluid; amplifying or signal amplifying in a qualitative or quantitative fashion and in a sequential or concurrent manner, two or more RNA species or cDNA derived therefrom, comprising a fraction of the extracted RNA; detecting the amplified or signal amplified product; whereby cancer or premalignancy is detected, diagnosed, evaluated, characterized, or monitored.

In particularly preferred embodiments of the invention, the bodily fluid is blood plasma or serum. Either fresh (i.e., never frozen) blood plasma or serum, or frozen (stored) and subsequently thawed plasma or serum may be used for purposes of these embodiments. In a preferred embodiments wherein stabilizing agent is not used, the blood is processed soon after drawing, preferably within 24 hours and most preferably within 6 hours, to minimize any degradation of nucleic acids. While early processing is not a requirement of the methods of the invention, it will be recognized that variations of early processing can be employed as set forth below, without limitation implied. In one aspect, the blood may be initially processed to stabilize the RNA or to stabilize phospholipids encapsulating the extracellular RNA, or to inhibit nucleases present in blood. Stabilizing agents or inhibitors may be provided within kits according to the invention or within venipuncture tubes or devices. Such initial processing is useful if specimen transport or work schedules will result in processing delays. In another aspect, initial processing may be performed by hybridizing the RNA or binding associated apoptotic bodies or other RNA encapsulated particles to solid substrates shortly after venipuncture, preferably using reagents provided in a kit of this invention or as part of specialized blood collection systems. It is preferred that the processing of the specimen from the human or animal subject and from the reference group or population be handled in a similar or like manner to the extent practical, or alternatively the effect due to variations in specimen processing defined and comparisons appropriately adjusted.

In a preferred embodiment, blood is first collected by venipuncture and may be kept on ice until serum or plasma is separated from whole blood, for example using centrifugation methods preferably gentle enough not to cause lysis or disruption of blood cells. While a considerable range of centrifugation speeds may be employed, centrifugation at high speeds (such as beyond 100,000×g) for prolonged periods should be avoided to prevent clearance of RNA-containing apoptotic bodies or other encapsulated extracellular RNA particles from the supernatant. Non-limiting examples of suitable conditions is centrifuging a blood specimen at a range of 300 to 5,000×g for five to thirty minutes, or fractionating by other standard methods to produce plasma or serum will suffice. Sera or plasma obtained in this manner can be assayed directly or stored frozen, for example at −20 to −80 degrees centigrade until further analysis according to the methods of this invention.

In a preferred embodiment, RNA in plasma, serum, or bodily fluid is stabilized against RNase by mixing the plasma, serum, or bodily fluid with an RNase inhibitor agent or RNase inactivator. The plasma or serum may be mixed with the stabilizing agent shortly following venipuncture. Alternatively, the plasma or serum may be mixed with the stabilizing agent following filtration, centrifugation or clotting. It is most preferred but not required that plasma or serum be mixed with the stabilizing agent within 6 hours of blood draw. In a preferred embodiment, the plasma or serum RNA so stabilized is total RNA, a portion of which comprises non-mutated RNA. In one aspect a portion of said RNA further comprises a coding RNA and/or a non-coding RNA. RNase inhibitor or inactivating agents are known to the art, including commercially available agents, and may be utilized as stabilizing agent. In a particularly preferred embodiment, plasma or serum is mixed 1:1 with Trizol (Life Technologies, Carlsbad, Calif.) as a stabilizing agent.

The stabilizing agent may be provided within a kit to be used for the stabilization of extracellular RNA. The components of the kit would include a stabilizing agent such as Trizol or similar RNase inhibitor, usually of a predetermined amount, and may further may include one or more additional kit components including but not limited by a tube or vacutainer tube for venipuncture, wherein said vacutainer tube may or may not contain the stabilizing agent, RNA extraction agent, primers or probes to specific RNA or cDNA species, reagents for amplification or reverse transcription; and/or RNA reference specimen.

The invention further encompasses other stabilizing agents that stabilize or protect plasma, serum, or bodily fluid extracellular RNA from RNase. In a preferred embodiment, the stabilizer agent hybridizes to specific RNA species, thereby stabilizing the RNA against nucleases. In another preferred embodiment, the stabilizer agent is a protein that binds to the RNA species in a manner that stabilizes the RNA species against degradation by RNase. In another preferred embodiment of the invention, the stabilizer agent increases the stability of a phospholipid membrane, thereby stabilizing the particle or apoptotic body encapsulating extracellular RNA in plasma, serum, or bodily fluid. In another embodiment, the stabilizer agent promotes aggregation of particles or apoptotic bodies encapsulating extracellular RNA in plasma or serum or bodily fluid. The stabilizing agent may be a coated bead or particle, or a coated solid surface. Similarly, kits comprising the stabilizer agent, as described above, which may further include one or more additional kit components including but not limited to a vacutainer tube for venipuncture, wherein said vacutainer tube may or may not contain the stabilizing agent, RNA extraction agent, primers or probes to specific RNA or cDNA species, reagents for amplification or reverse transcription, and/or an RNA reference specimen.

In a preferred embodiment of the invention, extracellular RNA in plasma or serum or other bodily fluid of the human or animal is assayed by extracting total extracellular RNA from plasma or serum or other bodily fluid of the human or animal, determining quantitatively or qualitatively the amount or concentration of total extracellular RNA, or one or a plurality of specific RNA species thereof comprising a portion of the total extracellular RNA, and comparing said amount or concentration obtained from the human or animal to the total extracellular RNA, or one or a plurality of specific RNA species thereof from a reference group, wherein said comparison detects, diagnoses, infers, or monitors a disease, particularly cancer or neoplastic disease in the human or animal. Bodily fluids are preferably separated into essentially cellular and non-cellular components, using centrifugation or other fractionation techniques, and total extracellular RNA thereafter extracted from the non-cellular components.

In the practice of the methods of this invention, total extracellular RNA can be extracted from bodily fluid using methods well-known to the art, including but not limited to gelatin extraction method; silica, glass bead, or diatom extraction method; guanidinium thiocyanate acid-phenol based extraction methods; guanidinium thiocyanate acid based extraction methods; centrifugation through a cesium chloride or similar gradient; phenol-chloroform based extraction methods; hybridization and immunobead separation; or commercially available RNA extraction methods. Methods of RNA extraction are further provided in U.S. Pat. No. 6,329,179 B1, incorporated herein in its entirety by reference. If plasma or serum had been previously frozen, upon assay it should be thawed rapidly, for example in a warm water bath at about 37 degrees centigrade, and thereafter RNA rapidly extracted to minimize degradation thereof.

However, it should be understood that extraction of total extracellular RNA is not a requirement for the practice of the methods of this invention. In some embodiments, methods such as spectroscopic methods including mass spectroscopy, and cytometry can be used for direct analysis of total extracellular RNA or RNA encapsulated particles within the bodily fluid.

The amount or concentration of total extracellular RNA from the bodily fluid is determined quantitatively or qualitatively using nucleic acid (RNA or cDNA) amplification, signal amplification, spectroscopy including mass spectroscopy, or hybridization to a detectably-labeled probe. In a preferred embodiment, a portion of the extracted total extracellular RNA is amplified or signal amplified qualitatively or quantitatively. Total extracellular RNA extracted from blood plasma or serum or other bodily fluid may first be reverse transcribed to cDNA, whereupon the cDNA is amplified or signal amplified qualitatively or quantitatively. In preferred embodiments, amplification is performed using primers or probes that are specific for particular RNA or cDNA species, wherein the RNA or its cDNA may be a non-tumor related RNA or a tumor-related RNA. Non-tumor RNA include but are not limited to housekeeper gene RNA, and non-limiting examples of non-tumor RNA include RNA encoding all or a portion of c-abl, porpho-bilinogen deaminase (PBDG), glyceraldehyde 3-phosphate dehydrogenase (GAPDH), retinoic acid receptor (RAR), and beta-actin. Examples of tumor-related or tumor-associated RNA not intending to be limiting include tyrosinase RNA, keratin RNA species, prostate specific antigen RNA, alpha-fetoprotein RNA, BCR/abl RNA, carcinoembryonic antigen RNA, p97 RNA, p16 RNA, MUC 18 RNA, PML/RAR RNA, CD44 RNA, EWS/FLI-1 RNA, EWS/ERG RNA, AML1/ETO RNA, MAGE RNA species, beta human chorionic gonadotropin RNA, telomerase-associated RNA including TEP1 RNA, human telomerase RNA template (hTR) RNA and telomerase reverse transcriptase protein (hTERT) RNA, bcl-2 RNA, bax RNA, survivin RNA, COX-2 RNA, P53 RNA, c-myc RNA, her-2/neu RNA, Von Hippel-Lindau gene RNA, retinoblastoma gene RNA, mutated in colon cancer (MCC) gene RNA, adenomatous polyposis coli (APC) gene RNA, deleted in colon cancer (DCC) gene RNA, epidermal growth factor receptor (EGFR) RNA, epidermal growth factor (EGF) RNA, hn RNP-A1

RNA, hn RNP-A2/B1 RNA, hn RNP-K RNA, 5T4 RNA, DNA methyltransferase RNA, matrix metalloproteinase species RNA, mammaglobin RNA, DD3(PCA3) RNA, glutathione S-transferase RNA, MDR-1 RNA, and JC virus RNA. It will be recognized that the above examples are not intended to be limiting, and any non-tumor or tumor-related RNA species or corresponding cDNA may be detected according to the methods of this invention. Further, it will be recognized that various RNA species are well known to the art, and that the scope of the invention is meant to encompass these RNA species without limitation.

Various amplification methods or signal amplification methods are known in the art and can be used in accordance with the methods of this invention. In preferred embodiments of the methods of the invention, quantitative or qualitative amplification is performed using an amplification or signal amplification method such as polymerase chain reaction; reverse transcriptase polymerase chain reaction; ligase chain reaction; DNA or RNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; or any combination or variation thereof. In one aspect of this embodiment, quantitative amplification is performed using the Taqman technology (Perkin Elmer Biosystems), with primers for the target RNA using a dye-labeled internal primer.

In preferred embodiments, following amplification the RNA or cDNA amplified or signal amplified product is detected in a quantitative or qualitative manner by methods known to the art. In preferred embodiments of the inventive methods, detection of amplified RNA or cDNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; Northern blot analysis; electrochemiluminescence; reverse dot blot detection; and liquid chromatography, including high-performance liquid chromatography.

Upon amplification and detection of total extracellular RNA or one or a plurality of specific RNA species, most preferably wherein one or a plurality of species of total extracellular RNA is a disease- or tumor-related gene, an amount or concentration or other value allowing comparative assessment is determines, using for example, gel intensity, signal intensity, or color intensity, color, mass, or electrical propensity. Assessment is made to a reference individual, group, or population based upon analysis of said RNA under similar condition and methods, or by extrapolation to similar conditions and methods. If the RNA in the subject specimen is of greater amount, concentration, or other assessment value than that expected for a healthy reference group or population, or within the range for a disease group or population, most preferably a cancer group or population, then disease, most particularly cancer or neoplastic disease, will be thereby diagnosed, detected, inferred, or monitored in the subject human or animal.

In another embodiment of the invention, determination of an amount, concentration, or other comparative assessment is made using total extracellular RNA without amplification prior to detection. For example but not limitation, total extracellular RNA extracted from a bodily fluid may be hybridized and detected without amplification. In this aspect, it is particularly preferred but not required that the extracted RNA be concentrated upon extraction or upon separation from the bodily fluid, using for example immunobead capture or hybridization onto a solid substrate, to improve assay sensitivity. In another aspect of this embodiment, extracellular RNA is evaluated by spectroscopy, for example by mass spectroscopy or magnetic resonance spectroscopy, or by flow cytometry. In one aspect, fluorometric methods may be employed, for example as employed by Kamm and Smith (1972, *Clin. Chem.* 18: 519-522), said reference incorporated herein in its entirety.

The methods of the invention identify humans or animals bearing or at risk for developing malignancies including but not limited to tumors of breast, ovarian, lung, cervical, colorectal, gastric, pancreatic, bladder, endometrial, head and neck, brain, kidney, and esophageal tissues, as well as leukemias, lymphomas, melanoma, and sarcomas. The methods of the invention may further be utilized to identify humans or animals with premalignancy, including but not limited to colorectal adenoma, cervical dysplasia, cervical intraepithelial neoplasia (CIN), bronchial dysplasia, bronchial metaplasia, atypical hyperplasia of the breast, ductal carcinoma in-situ of the breast, atypical endometrial hyperplasia, prostatic intraepithelial neoplasia, and Barrett's esophagus. The methods of the invention may be applied to a subject of any age, race, ethnicity or gender, although it is preferred that the reference group or population include individuals of similar age (child, adult, elderly) and sex (male, female).

The invention permits detection, diagnosis, and monitoring of disease, particularly cancer and premalignancy, and identification of individuals at risk for developing disease, particularly cancer or neoplastic disease such as premalignancy, providing considerable clinical utility. The invention provides methods to identify, stratify, or select a human or animal that might benefit from a therapy, or from a further diagnostic test. The invention permits disease such as cancer to be monitored, including response to cancer therapies, by providing a marker to guide whether therapeutic effect has been achieved, or if more therapy is required, and to assess prognosis.

An advantageous application of the methods of this invention is to allow selection of humans or animals for cancer therapies including surgery, biotherapy, hormonal therapy, anti-sense therapy, monoclonal antibody therapy, chemotherapy, vaccines, anti-angiogenic therapy, cryotherapy, radiation therapy, and RNA inhibitor-directed therapies.

Another advantageous application of the methods of this invention is to provide an indicator of a relapsed cancer following therapy, or impending relapse, or treatment failure.

Another advantageous application of the methods of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination including PAP, and physical examination.

The invention further provides diagnostic and research kits that enable quantitative, qualitative or other comparative assessment of total RNA or of specific RNA species in plasma, serum, or other bodily fluids. In one aspect, a kit according to this aspect of the invention can provide a reference range for normal values or values that are disease-related under conditions that enable identification or selection of a human or animal with a disease, most particularly cancer or neoplastic disease. In another aspect kits of this invention provide reagents for extracting total extracellular RNA from the bodily fluid, or reagents and/or probes and primers for the amplification of said RNA, or reagents and materials for the detection of RNA product, or reagents for hybridization of RNA, or standards and controls for the analysis of the test, or reagents or devices or tubes for collecting, handling, or storage of the bodily fluid, or any combination or variation thereof, wherein further the reagents may be standardized to be comparable with reagents used to define RNA values for the reference population.

The methods of the invention and preferred uses for the methods of the invention are more fully illustrated in the following Examples. These Examples illustrates certain aspects of the above-described method and advantageous results. These Examples are shown by way of illustration and not by way of limitation.

Example 1

Comparative Analysis of Two Extracellular RNA Species, and Application of a Stabilizing Agent Comparative analysis for two tumor-related mRNA, Her-2/neu RNA and hTERT RNA, in plasma was to be evaluated in quantitative fashion in a human. Blood is to be drawn in a local laboratory facility using an EDTA containing vacutainer tube. Within 3 hours following venipuncture, the blood specimen is to be centrifuged at 3000×g for 15 minutes, and then Trizol 2 milliliters is to be added to 2 milliliters of plasma. The plasma specimen mixed with Trizol is then shipped to a central laboratory. Total RNA is to be extracted from plasma according to manufacturer's instructions using Trizol. The extracted RNA from 50 microliters of plasma was then reverse transcribed and Her-2/neu cDNA and hTERT cDNA amplified quantitatively using Taqman and using cDNA-specific primers. The amount or concentration of each RNA species is to be comparatively analyzed, thereby supporting a diagnosis of breast cancer. The assay is to be repeated serially throughout treatment thereby enabling the characterization of the cancer and monitoring response to therapy.

Example 2

Clinical Application

A 52 year-old woman with no symptomatic evidence of disease presents for routine cancer screening. Her physician draws a plasma specimen for assay. Total extracellular RNA is extracted from the patient's plasma, and the extracted extracellular RNA amplified quantitatively using Taqman PCR technology for a housekeeping gene RNA or similar standard RNA such as c-abl RNA, and for a tumor-associated RNA such as EGFr RNA. In this case the woman's quantitative levels of EGFr RNA are substantially elevated in comparison to an EGFr RNA reference standard for healthy patients without cancer, while levels of c-abl RNA are consistent with the normal reference range of c-abl RNA in plasma from healthy patients without cancer. The difference between the two ratios indicates that either the presence of cancer, or a high risk of developing cancer, is therefore identified for the woman.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of determining a ratio of the amount or concentration of an extracellular human RNA from plasma or serum from a human that is a coding RNA comprising an open reading frame encoding an amino acid sequence to the amount or concentration of an extracellular human RNA from said plasma or serum from said human that is a non-coding RNA, the method comprising the steps of:

a) obtaining plasma or serum from a blood specimen from a human;
   b) mixing the plasma or serum obtained from the blood specimen from the human with a RNase inhibitor agent and producing a plasma or serum mixture;
   c) extracting extracellular human RNAs from said plasma or serum mixture and producing extracted human RNAs, wherein a portion of the extracted human RNAs comprises said coding RNA and a portion of said extracted human RNAs comprises said non-coding RNA;
   d) amplifying said coding RNA from a portion of said extracted human RNAs comprising said coding RNA using primers or probes specific for said coding RNA, or cDNA therefrom and producing a first amplified product, and amplifying said non-coding RNA from a portion of said extracted human RNAs comprising said non-coding RNA using primers or probes specific for said non-coding RNA, or cDNA therefrom and producing a second amplified product; and
   e) determining the amount or concentration of the coding RNA or cDNA therefrom by assaying said first amplified product, and determining the amount or concentration of the non-coding RNA or cDNA therefrom by assaying said second amplified product, and thereby the ratio of the amount or concentration of the coding RNA to the amount or concentration of the non-coding RNA is determined.

2. The method of claim 1, wherein the human has cancer or premalignancy.

3. A method of determining a ratio of the amount or concentration of an extracellular human RNA from plasma or serum from a human that is a coding RNA comprising an open reading frame encoding an amino acid sequence to the amount or concentration of an extracellular human RNA from said plasma or serum from said human that is a non-coding RNA, the method comprising the steps of:

a) obtaining plasma or serum from a blood specimen from a human;
   b) extracting extracellular human RNAs from said plasma or serum, wherein a portion of said extracted human RNAs comprises said coding RNA and a portion of said extracted human RNAs comprises said non-coding RNA;
   c) amplifying said coding RNA from a portion of said extracted human RNAs comprising said coding RNA using primers or probes specific for said coding RNA, or cDNA therefrom and producing a first amplified product, and amplifying said non-coding RNA from a portion of said extracted human RNAs comprising said non-coding RNA using primers or probes specific for said non-coding RNA, or cDNA therefrom and producing a second amplified product and
   d) determining the amount or concentration of said coding RNA or cDNA therefrom by assaying said first amplified product, and determining the amount or concentration of the non-coding RNA or cDNA therefrom by assaying said second amplified product, and thereby the ratio of the amount or concentration of the coding RNA to the amount of the non-coding RNA is determined.

4. The method of claim 3, wherein the human has cancer or premalignancy.

5. The method of claim 3, wherein at least one of said extracellular human RNAs is a tumor-associated or tumor-derived RNA.

6. A method of determining a ratio of the amount or concentration of an extracellular human RNA from a non-cellular fraction of blood from a human that is a coding RNA having an open reading frame encoding an amino acid sequence to the amount or concentration of an extracellular human RNA from said non-cellular fraction of blood from said human that is a non-coding RNA, the method comprising the steps of:
   a) obtaining a non-cellular fraction of blood from a blood specimen from a human;
   b) mixing the said non-cellular fraction of blood from the human with a RNase inhibitor agent and producing a non-cellular fraction of blood mixture;
   c) extracting extracellular human RNAs from said non-cellular fraction of blood mixture, wherein a portion of the extracted human RNAs comprises said coding RNA and a portion of said extracted human RNAs comprises said non-coding RNA;
   d) amplifying said coding RNA from a portion of said extracted human RNAs comprising said coding RNA using primers or probes specific for said coding RNA, or cDNA therefrom and producing a first amplified product, and amplifying said non-coding RNA from a portion of said extracted human RNAs comprising said non-coding RNA using primers or probes specific for said non-coding RNA, or cDNA therefrom and producing a second amplified product; and
   e) determining the amount or concentration of the coding RNA or cDNA therefrom by assaying said first amplified product, and determining the amount or concentration of the non-coding RNA or cDNA therefrom by assaying said second amplified product, and thereby the ratio of the amount or concentration of the coding RNA to the amount or concentration of the non-coding RNA is determined.

7. The method of claim 6, wherein the non-cellular fraction of blood is plasma or serum.

8. The method of claim 6, wherein the human has cancer or a premalignancy.

9. The method of claim 6, wherein the coding RNA is a housekeeper gene RNA.

10. A method of determining a ratio of the amount or concentration of an extracellular human RNA from a non-cellular fraction of blood from a human that is a coding RNA having an open reading frame encoding an amino acid sequence to the amount or concentration of an extracellular human RNA from said non-cellular fraction of blood from said human that is a non-coding RNA, the method comprising the steps of:
   a) obtaining a non-cellular fraction of blood from a blood specimen from a human;
   b) extracting extracellular human RNAs from said non-cellular fraction of blood, wherein a portion of the extracted mammalian human RNAs comprises said coding RNA and a portion of said extracted human RNAs comprises said non-coding RNA;
   c) amplifying said coding RNA from a portion of said extracted human RNAs comprising said coding RNA using primers or probes specific for said coding RNA, or cDNA therefrom and producing a first amplified product, and amplifying said non-coding RNA from a portion of said extracted human RNAs comprising said non-coding RNA using primers or probes specific for said non-coding RNA, or cDNA therefrom and producing a second amplified product; and
   d) determining the amount or concentration of the coding RNA or cDNA therefrom by assaying said first amplified product, and determining the amount or concentration of the non-coding RNA or cDNA therefrom by assaying said second amplified product, and thereby the ratio of the amount or concentration of the coding RNA to the amount or concentration of the non-coding RNA is determined.

11. The method of claim 10, wherein the non-cellular fraction of blood is plasma or serum.

12. The method of claim 10, wherein the human has cancer or premalignancy.

13. The method of claim 10, wherein the coding RNA is a housekeeper gene RNA.

* * * * *